United States Patent [19]

Long et al.

[11] Patent Number: 4,777,131

[45] Date of Patent: Oct. 11, 1988

[54] METHOD OF DETERMINING SUGAR CONTENT OF TOBACCO USING A DISCRETE ANALYZER

[75] Inventors: Terence M. Long, Yatton; David J. Newman, Wrington, both of England; Susan J. Alsop, Chepstow, Wales

[73] Assignee: Imperial Tobacco Limited, Bristol, England

[21] Appl. No.: 2,933

[22] Filed: Jan. 13, 1987

[30] Foreign Application Priority Data

Jan. 13, 1986 [GB] United Kingdom ............... 8600679

[51] Int. Cl.$^4$ .................. C12Q 1/54; C12Q 1/48; C12Q 1/42; C12Q 1/32
[52] U.S. Cl. .................................. 435/14; 435/15; 435/18; 435/26; 436/131; 436/129; 436/128
[58] Field of Search ................. 436/128–131, 436/94–95; 435/14, 15, 18, 26

[56] References Cited

U.S. PATENT DOCUMENTS

| | | | |
|---|---|---|---|
| 3,838,010 | 9/1974 | Hammer | 435/26 |
| 3,875,011 | 4/1975 | Rubenstein et al. | 435/26 |
| 4,042,462 | 8/1977 | Johnson et al. | 435/15 |
| 4,097,338 | 6/1978 | Konttinen et al. | 435/26 |
| 4,118,279 | 10/1978 | Determann et al. | 435/4 |
| 4,120,755 | 10/1978 | Pierre et al. | 435/14 |
| 4,167,449 | 9/1979 | Gargiulo et al. | 435/24 |
| 4,309,502 | 1/1982 | Lauderdale | 435/26 |
| 4,371,611 | 2/1983 | Fusee | 435/26 |
| 4,438,199 | 3/1984 | Miwa et al. | 435/26 |
| 4,459,265 | 7/1984 | Berglund | 422/64 |
| 4,543,238 | 9/1985 | Mimura et al. | 422/64 |

FOREIGN PATENT DOCUMENTS 1144458 4/1983 Canada .
2023286 12/1979 United Kingdom .

OTHER PUBLICATIONS

"Chemical Abstracts" vol. 91, No. 23, 12/3/79, p. 356, col. 2, No. 189955H; Enzymic determination of glucose, fructose, and sucrose in tobacco. Sekin, Seval. Tob. Sci., 1979, 75–77.
Published European Patent Application No. 8,341A1 (Danninger, et al.), "Process for the Carrying Out of Enzymatic Determinations".

*Primary Examiner*—Barry S. Richman
*Assistant Examiner*—Timothy M. McMahon
*Attorney, Agent, or Firm*—Larson and Taylor

[57] ABSTRACT

A method of determining in a discrete analyzer the total sugars content of a tobacco sample containing sucrose, glucose and fructose, comprises the steps of, converting the sucrose to glucose and fructose, enzymatically converting the glucose and fructose to glucose-6-phosphate in the presence of hexokinase, reacting the glucose-6-phosphate with nicotinamide-adenine dinucleotide in the presence of glucose-6-phosphate dehydrogenase to give reduced nicotinamide-adenine dinucleotide, the amount of reduced nicotinamide-adenine dinucleotide produced being directly proportional to the total sugars content of the sample, measuring the concentration of reduced nicotinamide-adenine dinucleotide in the sample, and generating a signal indicative of the concentration of reduced nicotinamide-adenine dinucleotide and hence of the total sugars content of the sample. Deactivation of enzymes by any cyanogen bromide that may be present is prevented by the addition of dithioerythritol to the reaction mixture.

6 Claims, No Drawings

METHOD OF DETERMINING SUGAR CONTENT OF TOBACCO USING A DISCRETE ANALYZER

This invention concerns improvements in or relating to the chemical analysis of tobacco or smoking-related products, in particular for sugar content.

In the quality control of cigarettes or other smoking articles it has long been customary to carry out chemical analyses on auto-analyzers of tobacco and other smoking-related products such as filter rod material and cigarette paper. These analyses include analyses for naturally occurring sugars and nicotine in tobacco, glycerol triacetate (triacetin) in cellulose acetate abased filter rod material, and citrate salts, which are used as burn modifiers, in cigarette paper.

Hitherto, such analyses have been carried out by a number of laboratory technicians, each assigned to a separate analytical task. It is now proposed to carry out simultaneous chemical analyses of tobacco or tobacco-related products for a number of constituents by means of a discrete analyzer (one example of which being the Technicon RA-1000), such as is used in clinical analysis of physiological samples, but adapted to carry out chemical analyses peculiar to the tobacco industry. The use of a discrete analyzer enables analyses to be carried out simultaneously, more effectively, more accurately, and more consistently, on one machine, than can be carried out by a number of separate analytical processes and operators.

Although the discrete analyzer is designed to avoid cross-contamination as far as possible, in practice this is difficult to achieve completely, and so the chemical constitution of the reagents used must be such that interaction is minimal. Furthermore, discrete analysis is not a closed system and is open to airborne contamination.

Clearly, chemical analysis procedures hitherto used in the tobacco industry are, in general, quite unsuitable for use simultaneously on a discrete analyzer and so must either be modified or completely changed.

Sugars occur naturally in tobacco in the form of glucose, sucrose, and fructose. These have hitherto been determined in the laboratory by acid hydrolysis of sucrose to glucose and fructose, followed by reduction of potassium ferricyanide to ferrocyanide by the reducing sugars glucose and fructose. Quantitative reduction of ferricyanide takes place at 95° C., and, because a discrete analyzer is not able to operate at this temperature, it is not possible to use the analytical procedure described above on a discrete analyzer.

The nicotine content of tobacco and tobacco smoke has for many years been determined in the tobacco industry by a modification of the Konig reaction. In this reaction, cyanogen bromide splits the nicotine pyridine ring, and aniline reacts with the reaction product to give a yellow coloration the intensity of which, when monitored spectrophotometrically, is directly proportional to the nicotine content. The Konig reaction, when further modified, may be utilized in a discrete analyzer to determine nicotine content.

It is an object of the present invention to provide, for use in a discrete analyzer, a method of analysing tobacco or smoking-related products for sugar content. It is a further object of the invention to enable analyses for sugars and nicotine in tobacco to be carried out in a discrete analyzer without adverse interference between the reactions, and in particular to avoid adverse interference in the sugar analysis from cyanogen bromide used in nicotine analysis using a modified Konig reaction.

According to a first aspect of the present invention there is provided a method of determining in a discrete analyzer the total sugars content of a tobacco sample containing sucrose, glucose and fructose, the method comprising the steps of, (a) converting the sucrose to glucose and fructose, (b) enzymatically converting the glucose and fructose to glucose-6-phosphate in the presence of a first catalyst, (c) reacting the glucose-6-phosphate with nicotinamide-adenine dinucleotide in the presence of a second catalyst to give reduced nicotinamide-adenine dinucleotide, the amount of reduced nicotinamide-adenine dinucleotide produced being directly proportional to the total sugars content of the sample, (d) measuring the concentration of reduced nicotinamide-adenine dinucleotide in the sample, and (e) generating a signal indicative of the concentration of reduced nicotinamide-adenine dinucleotide and hence of the total sugars content of the sample.

The sucrose is preferably converted to glucose and fructose by means of an acid solution of invertase.

The enzymatic conversion of glucose and fructose to glucose-6-phosphate is preferably carried out by reacting the sample in the discrete analyzer, after the conversion of any sucrose present to glucose and fructose, with a neutral solution of adenosine-5-phosphate and phosphoglucose isomerase.

The first catalyst is preferably hexokinase.

The second catalyst is preferably glucose-6-phosphate dehydrogenase.

The concentration of reduced nicotinamide-adenine dinucleotide is preferably measured spectrophotometrically at a wavelength of 340 nm and a background correction made at 380 nm.

According to a second aspect of the present invention there is provided a method of determining in a discrete analyzer, in the presence of a Konig reaction using cyanogen bromide for the determination of nicotine in tobacco, the total sugars content of a tobacco sample containing sucrose, glucose and fructose, the method comprising carrying out the method according to the first aspect, characterised in that dithioerythritol is included in the reaction mixture of the first aspect, whereby the dithioerythritol protects the exzymes in said reaction mixture from deactivation by the cyanogen bromide without inhibiting either said enzymes or said Konig reaction.

It will be convenient to list the following abbreviations and their meanings as used in this specification.

HK—hexokinase
ATP—adenosine-5-phosphate
DTE—dithioerythritol
GP—glucose-6-phosphate
GPD—glucose-6-phosphate dehydrogenase
PGI—phosphoglucose isomerase
NAD—nicotinamide-adenine dinucleotide
NADH—reduced nicotinamide-adenine dinucleotide The invention will now be described with reference to the following non-limiting example.

An extraction solution A containing 1% acetic acid and 2% invertase concentrate was prepared by making 10 ml acetic acid and 20 ml invertase concentrate up to 1 litre with water. The invertase concentrate is a proprietary mixture of invertase, water and glycerol.

0.400 g of a tobacco sample were shaken with 100 ml of solution A for 20 minutes, and filtered to provide extract B prior to analysis on a discrete analyzer at ambient temperature.

During extraction of the tobacco by solution A, acetic acid removed from the nicotine from the tobacco into solution as nicotine acetate. Sucrose, glucose and fructose are all readily soluble in aqueous solvents, and all are brought into solution in the first two minutes of shaking. Invertase converts sucrose to glucose and fructose immediately it goes into solution, and conversion is complete in the shaking period. The conversion by invertase is optimum at pH 4.6 (i.e. weakly acidic). The mixture of tobacco/acetic acid is pH 4–5, although the pH of solution A before the tobacco is added is less than pH 4.

An aqueous solution C in distilled water of a proprietary glucose reagent by Technicon was made up to the following composition, one litre of C containing:
1.4 mmol of ATP
0.8 mmol of NAD
1000 U of HK
1000 U of GPD
10 mmol magnesium ion + buffers and stabilisers,
where 1 U = amount of enzyme to catalyse 1 micromole per minute, and 1 mol = molecular weight in g per litre.

A further solution D (sugar reagent) was prepared by adding the following to 100 ml of solution C:
100 microlitres of PGI
10 drops of a proprietary wetting agent (Technicon surfactant "W")
5.0 ml of 2% DTE solution.

In the discrete analyzer a 2.5 microlitre sample of extract B was added to 300 microlitres of solution D, and, after a delay of 7 minutes to allow the reaction producing NADH to proceed to completion, the concentration of NADH produced was measured spectrophotometrically at 340 and 380 nm, and a signal corresponding to the concentration of NADH sent to a microcomputer for further processing.

For calibration purposes the same overall procedure was carried out on samples of known sugar concentration. The amount of NADH produced by the reaction is proportional to the amount of sugar present in the sample presented for analysis. Hence by comparing the NADH reading of extract B with the sugar calibration solutions the sugar content of the tobacco sample for analysis is calculated by the microcomputer and the result printed.

As mentioned above, the discrete analyzer carries out an analysis for nicotine while it is carrying out the sugar analysis. The nicotine analysis involves the use of cyanogen bromide and, despite design features to prevent cross-contamination of the reactions, there is still sufficient residual carry-over of cyanogen bromide to cause enough enzyme inhibition to render the sugar analysis unreliable. It is found according to the invention that the addition of DTE to the enzyme mixture in the sugar analysis protects the sugar enzymes from deactivation without inhibiting either the sugar measurement enzymes or the cyanogen bromide used in the nicotine analysis.

The efficacy of the method of the invention was compared with that of a hitherto known method (Auto-Analyser) using statistical techniques. In this comparison 'DA' will be taken to mean a Discrete Analyser, and 'AA' will be taken to mean an Auto-Analyser.

50 individual tobacco samples were chosen for assessment of percentage content of sugar. These sample tobaccos covered a range of flue, oriental and air cured varieties containing from 0.1 to 7% nicotine and 0 to 35% sugar.

Bulks of each tobacco type were chosen to be sufficient to allow a total of eight random order analyses by both the DA and the AA.

Each tobacco bulk sample was milled as a whole and divided randomly into eight sub-samples. From each sub-sample, test samples (for each nicotine and sugar separately) were prepared as follows and then analysed in random order on AA and DA as appropriate.

AA: 0.4 g were taken from the sub-sample and extracted with 100 ml dilute sulphuric acid.

DA: 0.4 were taken from the sub-sample and extracted with 25 ml dilute acetic acid-invertase.

The analytical results were statistically analysed for variance and analysis of variance (F-value with confidence limits). The statistical analyses are set out in Tables 1 and 2 and show that the consistency of the sugar-in-tobacco analyses performed by the Discrete Analyzer and the method of the invention is significantly better than the consistency of the corresponding analyses performed by the known method of the Auto-Analyzer.

TABLE 1

Variance of sugar-in-tobacco analyses as between Auto-Analyzer and Discrete Analyzer.

| AA | DA |
|---|---|
| 0.02611 | 0.02259 |

TABLE 2

Analysis oF variance in tobacco data between Auto-Analyzer and Discrete Analyzer (F-value and significance level).

| F-value | Sig. lev. |
|---|---|
| 39.33 | 0.1% |

We claim:

1. A method of determining in a discrete analyzer the total sugars content of a tobacco sample containing sucrose, glucose and fructose, said sample containing cyanogen bromide, the method comprising the steps of,
   (a) converting the sucrose to glucose and fructose,
   (b) enzymatically converting the glucose and fructose to glucose-6-phosphate in the presence of a first catalyst and in the presence of dithioerythritol to protect the enzyme(s) from the cyanogen bromide.
   (c) reacting the glucose-6-phosphate with nicotinamide-adenine dinucleotide in the presence of a second catalyst to give reduced nicotinamide-adenine dinucleotide, the amount of reduced nicotinamide-adenine dinucleotide produced being directly proportional to the total sugars content of the sample,
   (d) measuring the concentration of reduced nicotinamide-adenine dinucleotide in the sample, and
   (e) generating a signal indicative of the concentration of reduced nicotinamide-adenine dinucleotide and hence of the total sugars content of the sample.

2. The method as claimed in claim 1 wherein the sucrose is converted to glucose and fructose by means of an acid solution of invertase.

3. The method as claimed in claim 1 wherein the enzymatic conversion of glucose and fructose to glucose-6-phosphate is carried out by reacting the sample in the discrete analyzer, after the conversion of any sucrose present to glucose and fructose, with a neutral solution of adenosine-5-phosphate and phosphoglucose isomerase.

4. The method as claimed in claim 1 wherein the first catalyst is hexokinase.

5. The method as claimed in claim 1 wherein the second catalyst is glucose-6-phosphate dehydrogenase.

6. The method as claimed in claim 1 wherein the concentration of reduced nicotinamide-adenine dinucleotide is measured spectrophotometrically at a wavelength of 340 nm and a background correction made at 380 nm.

* * * * *